United States Patent [19]
Baumeister et al.

[11] Patent Number: 5,962,741
[45] Date of Patent: *Oct. 5, 1999

[54] PROCESS FOR THE PRODUCTION OF AROMATIC HALOGEN-AMINO COMPOUNDS

[75] Inventors: Peter Baumeister, Flüh; Urs Siegrist, Eiken; Martin Studer, Basel, all of Switzerland

[73] Assignee: Novartis AG, Basel, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/970,512

[22] Filed: Nov. 14, 1997

[30] Foreign Application Priority Data

Nov. 19, 1996 [CH] Switzerland ............... 2851/96

[51] Int. Cl.$^6$ ................. C07C 209/36
[52] U.S. Cl. ............... 564/417
[58] Field of Search ............... 564/417

[56] References Cited

U.S. PATENT DOCUMENTS

| | | | |
|---|---|---|---|
| 3,666,813 | 5/1972 | Hindin et al. | 260/580 |
| 3,944,615 | 3/1976 | Iqbal | 260/580 |
| 4,020,107 | 4/1977 | Kosak . | |
| 4,212,824 | 7/1980 | Seagraves . | |
| 5,856,578 | 1/1999 | Siegrist et al. | 564/423 |

FOREIGN PATENT DOCUMENTS

| | | |
|---|---|---|
| 0 002 308 | 6/1979 | European Pat. Off. . |
| 2 042 368 | 4/1971 | Germany . |
| 2 214 056 | 10/1973 | Germany . |
| 25 19 838 | 11/1976 | Germany . |
| 28 49 002 | 5/1980 | Germany . |
| 799871 | 8/1958 | United Kingdom . |
| 95 32941 | 12/1995 | WIPO . |
| 95 32952 | 12/1995 | WIPO . |

OTHER PUBLICATIONS

Marino, J.P. et al., Synthetic Communications, vol. 24, No. 6, 1994, pp. 839–848.
Rylander, P.N., Hydrogenation Methods, Academic Press, London, 1985, pp. 326–329.
Rylander, P.N., Catalytic Hydrogenation in Organic Synthesis, Academic Press, London, 1979, p. 140.
Rylander, P.N., Hydrogenation Methods, Academic Press, London, 1985, p. 77.
Freifelder, M., Practical Catalytic Hydrogenation, Wiley, New York, 1971, p. 256.
Freifelder, M., Practical Catalytic Hydrogenation, Wiley, New York, 1971, p. 306.
Tong et al., AICHE Loss Prev. 1997, (11), pp. 71–75.
J.R. Kosak, Catalysis in Organic Synthesis, vol. 18, 1988, pp. 135–147.
J.R. Kosak, Catalysis in Organic Synthesis, 1980, pp. 107–117.
Derwent Abstract, 86–046753 (1986) of SU 285689A.
Chem. Abstr. vol. 76:104258a (1972) of Bizhanov, et al.
Stoessel, F., J. Loss Prev. Process Ind., 1993, vol. 6, No. 2, pp. 79–85.
Miller, J.A., Cancer Research (1970) 30, pp. 559–576.

*Primary Examiner*—Brian M. Burn
*Attorney, Agent, or Firm*—Stephen G. Kalinchak

[57] ABSTRACT

The present invention relates to a hydrogenation process for the production of aromatic halogen-amino compounds by means of catalytic hydrogenation on noble metal catalysts of corresponding aromatic halonitro compounds, characterised in that a rhodium, ruthenium, iridium, platinum or palladium catalyst which is modified with an inorganic or organic phosphorus compound with a degree of oxidation of less than V, is used, in the presence of a vanadium compound.

16 Claims, No Drawings

PROCESS FOR THE PRODUCTION OF AROMATIC HALOGEN-AMINO COMPOUNDS

The present invention relates to a hydrogenation process for the production of aromatic halogen-amino compounds. Production is effected by means of catalytic hydrogenation of the corresponding aromatic halonitro compounds in the presence of a modified noble metal catalyst and a vanadium compound. The invention also relates to catalyst systems consisting of a modified noble metal catalyst and a vanadium compound, as well as the use thereof in the hydrogenation of aromatic halonitro compounds.

It is known that aromatic nitro compounds may be reduced to aromatic amines in very good yields in the presence of noble metal catalysts and hydrogen. When further hydrogenatable groups are present simultaneously, for example halogen substituents (halonitro aromatic substances), special measures are necessary to prevent the formation of undesired by-products, which otherwise can often only be separated from the desired product at great expense or, in particularly unfavourable cases, not at all. What is particularly difficult is selective reduction, if several hydrogenatable groups are present in a compound.

Catalytic hydrogenation of aromatic nitro compounds to the corresponding aromatic amines takes place via several intermediate steps. The corresponding nitroso compounds, and in particular the hydroxylamine intermediate step, are important. In practice, the formation of hydroxylamines is a special problem, since it can accumulate in large quantities in the reaction solution under certain conditions. This applies in particular to aromatic nitro compounds, the hydrogenation of which yields relatively stable arylhydroxylamines. This is especially critical if hydrogenation is carried out in a slurry-batch reactor. In extreme cases, several tons of arylhydroxylamine may be formed in the interim.

In U.S. Pat. No. 4,020,107, phosphorous acid, hypophosphorous acid or derivatives thereof are proposed as an additive in the hydrogenation of nitro-aromatic substances, which are substituted by halogen on the aromatic substance, using Pt or Pd on activated carbon and hydrogen. These systems are selective towards the halogen substituents present in the molecule. However, they have too little reactivity, which in many cases leads to the formation of considerable quantities of undesired arylhydroxylamines [J. R. Kosak, in Catalysis of Organic Reactions, Vol 18, (1988), 135–147); idem, in Catalysis in Organic Synthesis, 1980, 107–117].

The accumulation of arylhydroxylamines is undesired for the following reasons. On the one hand, it is known that such compounds are thermally unstable, and upon heating with or without $H_2$ may disproportionate whilst giving off heat. Further decomposition reactions may be initiated by the heat being released, and these then may consequently give rise to occurrences of severe explosions. W. R. Tong et al, AICHE Loss Prev. 1977, (11), 71–75 describe such an occurrence during the reduction of 3,4-dichloronitrobenzene to 3,4-dichloroaniline.

In addition, arylhydroxylamines are known as strong carcinogens and represent a certain potential danger. Larger quantities formed have to be disposed of at great expense.

A third range of problems is the production of the desired pure aromatic amine. If, during hydrogenation or at the end of the reaction, significant quantities of arylhydroxylamine are present, this may lead to condensation, thus forming undesired, dyed azo or azoxy products or higher molecular weight, deeply dyed condensation products. Since the quantity of arylhydroxylamine may change from batch to batch, the product quality obtained varies in purity and appearance. Thus, complicated purifying operations are necessary, with corresponding losses in yield and problems relating to disposal of the residue.

The above-mentioned problems are intensified in such a way that the concentrations occurring or even the maximum possible concentrations of this hydroxylamine intermediate step cannot be predicted even in the case of known processes which have been studied thoroughly. The presence of traces of impurities may unpredictably initiate the spontaneous accumulation of hydroxylamine intermediate steps. For example, J. R. Kosak, in Catalysis of Organic Reactions, Vol. 18, (1988), 135, describes that the simple addition of 1% $NaNO_3$ increases accumulation during hydrogenation of 3,4-dichloronitrobenzene from an original <5% to approximately 30%.

It has now surprisingly been found that the catalytic hydrogenation of aromatic halonitro compounds is effected with very high selectivity, with high yields and short reaction times, if rhodium, iruthenium, ridium, platinum or palladium catalysts, which are modified with inorganic or organic phosphorus compounds with a degree of oxidation of less than 5, are used in the presence of a vanadium compound.

Surprisingly, in many cases, only small concentrations of hydroxylamine occur. Normally, the hydroxylamine concentrations observed during the entire reaction are less than 1%. In this way, it is possible to use higher concentrations or quantities of halonitro aromatic substances, which contributes towards providing an extremely economical process without endangering the required safety measures. In addition, the activity and selectivity of the catalyst systems is high.

The catalyst systems may be easily produced for example from well known, commercially available standard noble metal catalysts, for example standard Pt, Pd or Ir hydrogenation catalysts, so that a constant quality of catalyst is assured, which is of importance for large-scale production.

Frequently, in hydrogenation, a lower pressure (ca. 5 bar) and a comparatively low temperature (ca. 100°) may even be used.

A further advantage of the process also over known reduction methods, such as Béchamp reduction or sulphide reduction, is that only small quantities of product residues are obtained, which have to be disposed of. The product is obtained in high purity, since practically no azo or azoxy compounds result, and the reaction may be carried out in a highly economic manner in current reactors without having to resort to special safety measures. Hydrogenation, especially the latter phase, is quick. The outcome of this is considerable advantages as regards constant quality.

The subject matter of the invention is a process for the production of aromatic halogen-amino compounds by means of catalytic hydrogenation of corresponding aromatic halonitro compounds on noble metal catalysts, characterised in that hydrogenation is carried out in the presence of a rhodium, ruthenium, iridium, platinum or palladium catalyst, which is modified with an inorganic or organic phosphorus compound with a degree of oxidation of less than 5, and in the presence of a vanadium compound.

Preferably, the noble metal catalyst employed is a platinum or iridium catalyst, most preferably a platinum catalyst.

The noble metal catalyst is preferably employed in a quantity of 0.1 to 10% by weight, most preferably in an amount of 0.1 to 2% by weight, based on the aromatic halonitro compound employed.

It is preferable to use a noble metal catalyst which contains 1 to 10% by weight platinum. The platinum employed may be applied to a carrier as platinum black, platinum oxide or preferably in metallised or oxidised form. Especially good carriers are activated carbon, silicon dioxide in the form of silicic acid or silica gel, aluminium oxide, calcium carbonate, calcium phosphate, calcium sulphate, barium sulphate, titanium oxide, magnesium oxide or iron oxide, most preferably activated carbon, aluminium oxide or silicon dioxide. Platinum applied to the above-mentioned carrier material is available commercially, or may be produced by methods which are familiar to a person skilled in the art, as disclosed for example in DE-OS 2 042 368.

Phosphorus compounds as modifiers may be in principle any inorganic or organic phosphorus compounds, in which the phosphorus has a degree of oxidation of less than 5. Examples are most preferably phosphorous acid and derivatives of phosphorous acid, as named for example in U.S. Pat. No. 4,020,107.

Examples of further phosphorus compounds that are suitable according to the invention are phosphines $P(R_a)_{3-n}(H)_n$, phosphites $P(OR_a)_3$, phosphinous acids $HO-P(H)_m(R_a)_{2-m}$, phosphine oxides $O=P(R_a)_{3-n}(H)_n$, hypophosphonous acids;

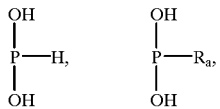

hypophosphorous acids $O=P(OH)(H)_m(R_a)_{2-m}$ and phosphorous acids $O=P(OH)_2H$ or $O=P(OH)_2R_a$, wherein $R_a$ signifies linear or branched $C_1$–$C_{12}$-alkyl or $C_6$–$C_{16}$-aryl, m is 0, 1 or 2, and n is 0, 1, 2 or 3, as well as the salts, esters and amides of the acids.

Examples of $C_1$–$C_{12}$-alkyl are methyl, ethyl, the various isomers of propyl, butyl, pentyl, hexyl, heptyl, octyl, nonyl, decyl, undecyl and dodecyl.

$C_6$–$C_{16}$-aryl may be unsubstituted or substituted phenyl, naphthyl, anthracyl, tetralin, indene, azuline or biphenyl.

$R_a$ is preferably $C_1$–$C_6$-alkyl or unsubstituted phenyl, or phenyl substituted by $C_1$–$C_6$-alkyl or $C_1$–$C_6$-alkoxy.

The phosphorus compounds, where they are acids, may exist as free acids, salts, esters or amides.

Preference is given to diphenylphosphine, triphenylphosphine, phosphinous acid and its salts, amides and esters, diphenylphosphinic acid, diphenylphosphite, phosphine oxides, phosphorous acid and its salts or esters, as well as hypophosphorous acid and its salts, amides and esters.

Especially preferred are phosphorous acid and its salts, amides and esters, as well as hypophosphorous acid and its salts, amides and esters.

The salts which may be mentioned are preferably those with cations from the group of alkali metals and alkaline earth metals, or the ammonium cation. Preferred alkali metals and alkaline earth metals are Li, Na, K, Ca or Mg.

The ammonium cation may be $NH_4^+$, $(C_1-C_6\text{-alkyl})_4N^+$ or an ammonium cation substituted with a mixture of H and $C_1$–$C_6$-alkyl.

Examples of $C_1$–$C_6$-alkyl are methyl, ethyl, the various isomers of propyl, butyl, pentyl or hexyl.

Modification of the noble metal catalysts may basically take place during or following the preparation process for the hydrogenation catalyst. However, it is preferably undertaken prior to adding the catalyst to the reaction mixture, or it is effected directly in the reaction mixture, for example whereby a phosphorus compound is added separately in either dissolved or dispersed form, and both are stirred together with the solution to be hydrogenated. It is also possible to set the pH value of the catalyst mixture to a certain value during modification, by adding acids or bases. It is similarly possible to first of all modify the noble metal catalyst with the phosphorus compound by mixing both together as solids, or by dissolving the phosphorus compound in a solvent and suspending the noble metal catalyst in the solution, and subsequently filtering. The modified catalyst may be stored and added to the solution to be hydrogenated as required.

Modification of the noble metal catalyst with the phosphorus compound is preferably effected prior to catalytic hydrogenation.

The phosphorus compound may be dissolved or dispersed in the reaction medium to be hydrogenated.

The ratio of noble metal in the noble metal catalyst to the modifying phosphorus compound is preferably 1: 0.1 to 1: 1000, most preferably 1:1 to 1:100 molar parts.

Vanadium compounds in terms of this invention are elementary vanadium or vanadium compounds in which the vanadium has a degree of oxidation of 0, II, III, IV or V.

The vanadium compounds may be dissolved or dispersed in the reaction medium in catalytic quantities.

Another variant of the process is obtained if the vanadium compound is mixed with the noble metal catalyst or applied to it. The noble metal catalyst may already be modified with the phosphorus compound or may be modified only afterwards. In principle, the vanadium compound may also be applied to the hydrogenation catalyst in the course of the preparation process of the hydrogen catalyst, before or after it is modified with a phosphorus compound.

One preferred variant is for the vanadium compound to be firstly applied to a suitable carrier material, and then dispersed in the reaction medium in this form together with the modified noble metal catalyst. Suitable carrier materials are for example all carrier materials that are used for the production of commercial powdered hydrogenation catalysts, as mentioned above. Activated carbon is especially suitable.

The vanadium compound is applied to the catalyst or the carrier material in a simple manner, for example by dissolving it, suspending the catalyst or the carrier material in the solution, and subsequently filtering.

If desired, while the vanadium compound is being applied, the pH value of the suspension may be set at the desired value by adding acids or bases.

If the vanadium compounds are not soluble in the reaction medium, they may also be mixed in dispersed, suspended form with the suspended catalyst, and filtered off together.

The vanadium compounds with the degree of oxidation 0, II, III, IV or V may be elementary vanadium and also purely inorganic compounds, however organic complexes with for example oxalate or acetyl acetonate are also possible.

Preference is given to vanadium compounds, such as $V_2O_5$, $V_2O_4$, vanadium(III)acetyl acetonate, vanadium(IV)oxyacetyl acetonate or those which represent the purely inorganic salt, oxo salt, or the hydrate of a purely inorganic salt or oxo salt. Examples are $VOCl_3$, $VCl_6^-$, $[VO(SCN)_4]^{2-}$, $VOSO_4$, $NH_4VO_3$, $VCl_3$, $VOCl$, $VCl_2$ or the corresponding halides with F or Br.

Depending on the pH value, the compounds may be present in aqueous solution in various hydrate forms.

The vanadates with a degree of oxidation V, or the hydrates of these vanadates, as well as vanadium(III) acetyl acetonate, vanadium(IV)oxyacetyl acetonate are especially preferred, and vanadium(III) acetyl acetonate, vanadium (IV)oxyacetyl acetonate are preferred in particular.

Of the vanadates, ammonium, Li, Na or K vanadates, or the hydrates of these vanadates are preferred.

The molar ratio of noble metal in the noble metal catalyst to vanadium compound is preferably 1:0.1 to 1:1000, most preferably 1:1 to 1:50.

By the expression aromatic nitro and amino compounds in the course of the present invention are understood those systems which respond to the Hückels 4n+2 electron rule, for example aromatic hydrocarbons such as benzenes, polycyclic hydrocarbons (also partly hydrogenated such as tetralin), biphenyls, cyclopentadienyl anion and cycloheptatrienyl anion, anthraquinones, heteroaromatic substances such as pyridines, pyrroles, azoles, diazines, triazines, triazoles, furans, thiophenes and oxazoles, condensated aromatic substances such as naphthalene, anthracene, indoles, quinolines, isoquinolines, carbazoles, purines, phthalazines, benzotriazoles, benzofurans, cinnolines, quinazoles, acridines and benzothiophenes. The halogen and nitro groups are preferably bound to C-atoms of the aromatic nucleus.

The aromatic halonitro compounds may contain one or several nitro groups. They preferably contain one or two one or two nitro groups. The aromatic halonitro compounds may contain one or several, same or different halogen atoms, preferably one to three halogen atoms. The preferred halogen is chlorine and bromine.

The aromatic halonitro compounds may contain further substituents, preferably those without carbon/carbon and carbon/hetero atom multiple bonds.

The aromatic halonitro compounds of formula I most preferably correspond to formula I

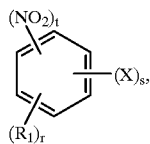

(I)

wherein
R$_1$ signifies hydrogen, C$_1$–C$_{12}$-alkyl, C$_1$–C$_{12}$-halogen-alkyl, C$_6$–C$_{16}$-halogen-aryl, C$_3$–C$_6$-halogen-heteroaryl, C$_1$–C$_4$-alkylphenyl, C$_1$–C$_4$-alkoxyphenyl, halogen-C$_1$–C$_4$-alkylphenyl, halogen-C$_1$–C$_4$-alkoxyphenyl, C$_1$–C$_{12}$-hydroxyalkyl, C$_3$–C$_8$-cycloalkyl, C$_3$–C$_8$-cycloalkyl substituted by C$_1$–C$_4$-alkyl, C$_6$–C$_{16}$-aryl, C$_7$–C$_{16}$-aralkyl, C$_3$–C$_6$-heterocycloalkyl, C$_3$–C$_{16}$-heteroaryl, C$_4$–C$_{16}$-heteroaralkyl, SO$_3$H, SO$_2$R$_2$, SO$_2$N(R$_2$)$_2$, or a group-Y$_1$R$_2$;
Y$_1$ signifies NR$_2$, oxygen or sulphur;
R$_2$ signifies hydrogen, C$_1$–C$_{12}$-alkyl, C$_1$–C$_{12}$-halogen-alkyl, C$_6$–C$_{16}$-halogen-aryl, C$_3$–C$_{16}$-halogen heteroaryl, C$_1$–C$_4$-alkylphenyl, C$_1$–C$_4$-alkoxyphenyl, halogen-C$_1$–C$_4$-alkylphenyl, halogen-C$_1$–C$_4$-alkoxyphenyl, C$_1$–C$_{12}$-hydroxyalkyl, C$_3$–C$_8$-cycloalkyl, C$_6$–C$_{16}$-aryl, C$_7$–C$_{16}$-aralkyl, C$_3$–C$_6$-hetercycloalkyl, C$_3$–C$_{16}$-heteroaryl, C$_4$–C$_{16}$-heteroaralkyl;
X signifies fluorine, chlorine, bromine or iodine; and
r,s and t, independently of one another, signify a number 1, 2 or 3, whereby r+s+t is less than or equal to six.
Preferably, r, s and t, independently of one another, are 1 or 2.

In the above definitions, halogen is understood to be fluorine, chlorine, bromine or iodine. Where there are several halogen substituents, these may be of the same type or mixed (for example Cl and F).

Alkyl may be methyl, ethyl, isopropyl, n-propyl, n-butyl, iso-butyl, sec.-butyl, tert.-butyl, as well as the various isomeric pentyl, hexyl, heptyl, octyl, nonyl, decyl, undecyl and dodecyl radicals.

Halogen-alkyl is for example fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is for example methoxy, ethoxy, propyloxy, i-propyloxy, n-butyloxy, i-butyloxy, s-butyloxy and t-butyloxy; preferably methoxy and ethoxy.

Halogen-alkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy; preferably difluoromethoxy, 2-chloroethoxy and trifluoromethoxy.

Cycloalkyl and alkyl-substituted cycloalkyl are for example cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

Alkoxyalkyl is e.g. methoxymethyl, ethoxymethyl, propyloxymethyl, methoxyethyl, ethoxyethyl, propyloxyethyl, methoxypropyl, ethoxypropyl or propyloxypropyl.

Phenyl, also as part of a substituent such as phenoxy, phenylthio, phenoxycarbonyl, phenylaminocarbonyl, benzyl or benzoyl, may in general be unsubstituted or may be substituted by further substituents. The substituents may then be in ortho-, meta- and/or para-position. Preferred substitution positions are the ortho- and para-position to the ring attachment site. Preferred substituents are halogen atoms.

Aralkyl is preferably C$_1$–C$_4$-alkyl substituted by phenyl, and signifies for example benzyl, phenethyl, 3-phenylpropyl, α-methylbenzyl, phenbutyl and α,α-dimethylbenzyl.

Aryl and analogously halogen-aryl are for example phenyl, tetralinyl, indenyl, naphthyl, azulenyl and anthracenyl.

Heteroaryl and analogously halogen-heteroaryl are for example radicals of pyrrole, furan, thiophene, oxazole, thiazole, pyridine, pyrazine, pyrimidine, pyridazine, indole, purine, quinoline and isoquinoline.

Hererocycloalkyl signifies for example radicals of oxirane, oxetane, azetidine, azirine, 1,2-oxathiolane, pyrazoline, pyrrolidine, piperidine, piperazine, morpholine, dioxolane, tetrahydropyran, tetrahydrofuran and tetrahydrothiophene.

Examples of preferred halonitro aromatic substances are o-, m- or p-nitrochlorobenzene, o-, m- or p-nitrobromobenzene, o-, m- or p-nitrofluorobenzene, 2-chloro-4-nitrotoluene, 2-bromo-4-nitrotoluene, 4-chloro-2-nitrotoluene, 4-bromo-2-nitrotoluene, 6-chloro-2-nitrotoluene, 3-chloro-4nitroethylbenzene, 2,5-, 2,3-, 2,4-, 3,4- or 3,5-dichloronitrobenzene, 3,4- or 2,4-dibromonitrobenzene, 4-chloro-6-nitrometaxylene, 3-chloro-4-nitropropylbenzene, 3-chloro-4-nitrobutylbenzene, 1-chloro-8-nitronaphthalene, 1-chloro-2-nitronaphthalene, 1-nitro-5,8-dichloronaphthalene, 3-chloro-4-fluoronitrobenzene, 2-fluoro-4-chloronitrobenzene, 2,4-difluoronitrobenzene, 2,4,5-, 2,3,5- or 2,4,6-trichloronitrobenzene,

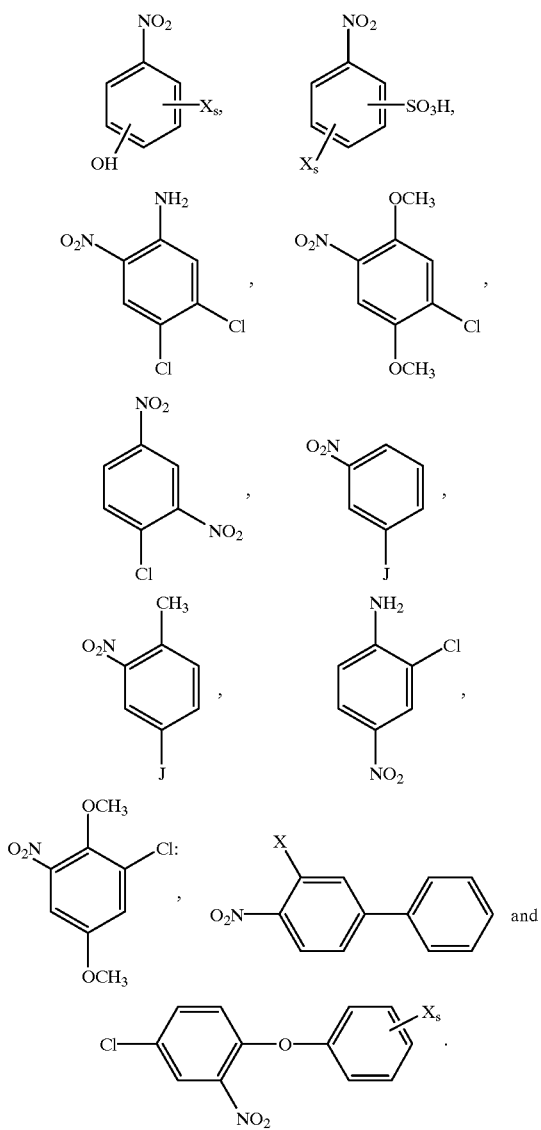

The process according to the invention may be effected at a pressure of 1 to 100 bar, preferably at a pressure of 1 to 40 bar, and most preferably at a pressure of 1 to 20 bar.

The temperature may be from 0° to +160° C. It is preferably +20° to +140° C., most preferably +20° to +100° C.

If the halonitro compound to be hydrogenated is liquid at the reaction temperature, hydrogenation may be carried out without solvents, or if the resulting amino compound is liquid under reaction conditions, these may serve as the solvent.

However, it is also possible to add inert solvents. Suitable solvents are for example water, alcohols such as methanol, ethanol, n-propanol, i-propanol, n-butanol, the isomeric butanols and cyclohexanol; ethers, esters and ketone, for example diethylether, methyl-tertiary-butyl-ether, tetrahydrofuran, dioxane, dimethoxyethane, acetic acid ethyl ester, acetic acid butyl ester, butyrolactone, acetone, methyl ethyl ketone, methyl-i-butyl ketone or cyclohexanone, carboxylic acids such as acetic acid and propionic acid, dipolar-aprotic solvents such as dimethyl formamide, N-methylpyrrolidone, dimethyl acetamide, sulpholane, dimethyl sulphoxide or acetonitrile, apolar solvents such as toluene or xylene, chlorinated aromatic hydrocarbons, such as also methylene chloride, $C_3$–$C_7$-alkanes or cyclohexane.

These solvents may be used alone or as mixtures of at least two solvents. In an especially preferred embodiment of the process according to the invention, the solvents employed are water, methanol, ethanol, iso-propanol, tetrahydrofuran, toluene, xylene in pure form or as mixtures with the above-mentioned solvents, especially with alcohols and/or $C_1$–$C_4$-carboxylic acids.

The pH value may be set at a certain value, as required, by adding bases or acids.

If solvents are used, the concentration of nitro aromatic substance in the solution is preferably 5 to 50% by weight, most preferably 10 to 30% by weight.

The reaction according to the invention is preferably carried out in the liquid phase, especially with a powdered catalyst, either continuously or discontinuously, as slurry phase hydrogenation or in a bubble-tray column or with a formed catalyst in a trickling bed. The reaction may also be carried out in the gas phase with a powdered catalyst in a fluidised bed or with a formed catalyst in a fixed bed.

The aromatic halo-amino compounds which may be produced by the process according to the invention are valuable intermediate products in the production of for example dyestuffs or pesticides.

A further object of the invention is the use of a composition, consisting of a rhodium, ruthenium, iridium, platinum or palladium catalyst, which is modified with an inorganic or organic phosphorus compound with a degree of oxidation of less than 5, and a vanadium compound, for the catalytic hydrogenation of aromatic halonitro compounds.

Another object of the invention is a composition, consisting of a rhodium, ruthenium, iridium, platinum or palladium catalyst, which is modified with an inorganic or organic phosphorus compound with a degree of oxidation of less than V, and a vanadium compound.

The embodiments, preferences and significances described more fully for the process according to the invention similarly apply to the use and the composition.

The following examples illustrate the invention.

EXAMPLE $A_1$

Impregnation of Activated Carbon With Ammonium Vanadate 300 mg of ammonium vanadate and 600 ml of deionised water are placed in an agitator vessel. Afterwards, 20 g of activated carbon are added and stirred for 30 minutes. The impregnated activated carbon is subsequently filtered off and washed in portions with 600 ml of deionised water. Finally, the vanadium-containing carbon is dried in a vacuum drying chamber at 60° C. until reaching a constant weight. 18.8 g of modified carbon with a vanadium content of 13.6 mg/g are obtained.

EXAMPLE $B_1$

Preparation of para-chloraniline 48 g of p-chloronitrobenzene and 20 mg of a vanadium-containing activated carbon produced according to example $A_1$ are mixed in an agitator autoclave.

300 mg of Pt-carbon catalyst (1 % platinum on activated carbon carrier) and 50 ml of methanol are placed in a separate glass container, and 3 ml of an aqueous stock solution containing 825 mg of hypophosphorous acid (content 50%) are added dropwise whilst stirring. After stirring for 15 minutes, the catalyst suspension is flushed into the autoclave with an additional 50 ml of methanol.

Hydrogenation takes place at 80° C. and 40 bar hydrogen pressure. The reaction is complete after ca. 1 hour. After 50% of the theoretical hydrogen has reacted, a sample is taken. In thin-layer chromatography, less than 1% of the hydroxylamine stage is detected. After cooling and rendering the autoclave inert with argon, the catalyst is filtered off and washed with a little methanol. After evaporating the solvent and subsequently drying, 37.6 g of p-chloroaniline (crude yield 99.6% of theory) are obtained.

EXAMPLE $B_2$
Preparation of 2-chloroaniline 1 g of Pt/C catalyst (5%) and 2 g of water are placed in a beaker and mixed with 0.21 g of aqueous $H_3PO_2$ solution (50% by weight, corresponding to 5% by weight phosphorus, based on the catalyst). The mixture is stirred for 10 minutes at room temperature, then 0.159 g of vanadylacetyl acetonate $VO(acac)_2$ are added and stirred for a further 5 minutes.

47.3 g of 1-chloro-2-nitrobenzene (0.3 moles) and 57 g of toluene are placed in an agitator autoclave, and the catalyst suspension is flushed in with 4.2 g of water. Hydrogenation subsequently takes place for 2 hours at a temperature of 100° C. and at a hydrogen pressure of 5 bar. After 30%, 50% and 70% of the theoretical hydrogen has reacted, a sample is taken. In $^H$NMR, less than 1% hydroxylamine intermediate stage is detected. After cooling and rendering the agitator autoclave inert with nitrogen, the catalyst is filtered off and rinsed with toluene. After working up by distillation, 37 g of 2-chloroaniline (yield 96.6% of theory) are obtained.

$^1$H-NMR ($CDCl_3$, 250 MHz): 4.05 ppm (s,2H); 6.65 ppm (m,1H); 6.75 ppm (m, 1H); 7.05 ppm (m, 1H); 7.23 ppm (m, 1H).

Example $B_3$
Preparation of 3,5-diamino-4-chloro-benzotrifluoride 0.48 g of Pt/C catalyst (5%) and 1.5 g of water are placed in a beaker and mixed with 103 mg of aqueous $H_3PO_2$ solution (50% by weight, corresponding to 5% by weight phosphorus, based on the catalyst). The mixture is stirred for 10 minutes at room temperature, then 77 mg of vanadylacetyl acetonate $VO(acac)_2$ are added and stirred for a further 5 minutes. 40 g of 4-chloro-3,5-dinitrobenzotrifluoride and 47 g of toluene are placed in an agitator autoclave, and the catalyst suspension is flushed in with 4 g of water. Hydrogenation subsequently takes place at a temperature of 100° C. and at a hydrogen pressure of 5 bar. When the hydrogen uptake is complete, the autoclave is cooled and rendered inert with nitrogen. The catalyst is filtered off and washed with toluene. After working up by distillation, 29.8 g of 3,5-diamino-4-chloro-benzotrifluoride (yield 95.8% of theory) are obtained. Elementary analysis:
calculated: C 39.93%; H 2.87%; N 13.3%; Cl 16.84%; F 27.07% found: 40.24%; 2.91%; 13.2%; 16.44%; 27.09%

EXAMPLE $B_4$
Preparation of 2-bromoaniline 0.48 g of Pt/C catalyst (5%) and 1.5 g of water are placed in a beaker and mixed with 103 mg of aqueous $H_3PO_2$ solution (50% by weight, corresponding to 5% by weight P, based on the catalyst). The catalyst mixture is stirred for 10 minutes at room temperature. Subsequently, 77 mg of vanadylacetyl acetonate $VO(acac)_2$ are added and stirred for a further 5 minutes. 29.9 g of 1-nitro-2-bromobenzene and 69 g of toluene are placed in an agitator autoclave, and the catalyst suspension is flushed in with 4 g of water. Hydrogenation subsequently takes place at a temperature of 100° C. and at a hydrogen pressure of 5 bar. When the hydrogen uptake is complete, the autoclave is cooled and rendered inert with nitrogen. The catalyst is filtered off and washed with toluene. After working up by distillation, 23.8 g of 2-bromoaniline (yield 93.7% of theory) are obtained.

$^1$H-NMR ($CDCl_3$, 250MHz): 4.08 ppm (s,2H); 6.62 ppm (m,1H); 6.76 ppm (m, 1H); 7.1 ppm (m, 1H); 7.4 ppm (m, 1H).

EXAMPLE $B_5$
Preparation of 3-amino-6-chloropyridine 0.18 g of Pt/C catalyst (5%) and 1.5 g of water are placed in a beaker and mixed with 40 mg of aqueous $H_3PO_2$ solution (50% by weight, corresponding to 5% by weight phosphorus, based on the catalyst). The catalyst mixture is stirred for 10 minutes at room temperature. Subsequently, 30 mg of vanadylacetyl acetonate $VO(acac)_2$ are added and stirred for a further 5 minutes.

18.3 g of 2-chloro-5-nitropyridine and 70 g of toluene are placed in an agitator autoclave, and the catalyst suspension is flushed in with 4 g of water. Hydrogenation subsequently takes place at a temperature of 100° C. and at a hydrogen pressure of 5 bar. When the hydrogen uptake is complete, the autoclave is cooled and rendered inert with nitrogen. The catalyst is filtered off and washed with toluene. After working up by distillation, 10.4 g of 3-amino-6-chloropyridine are obtained in a good yield and with excellent purity.

$^1$H-NMR ($CDCl_3$, 250MHz): 3.7 ppm (s,2H); 6.96 ppm (m,1H); 7.1 ppm (m, 1H); 7.85 ppm (m, 1H).

EXAMPLE $B_6$
Preparation of 3,4-dichloroaniline 0.22 g of Pt/C catalyst (5%) and 1.5 g of water are placed in a beaker and mixed with 48 mg of aqueous $H_3PO_2$ solution (50% by weight, corresponding to 5% by weight phosphorus, based on the catalyst). The catalyst slurry is stirred for 10 minutes at room temperature, and subsequently 36 mg of vanadylacetyl acetonate $VO(acac)_2$ are added and stirred for a further 5 minutes.

22.1 g of 3,4-dichloro-nitrobenzene and 70 g of toluene are placed in an agitator autoclave, and the catalyst suspension is flushed in with 4 g of water. Hydrogenation subsequently takes place at a temperature of 100° C. and at a hydrogen pressure of 5 bar. When the hydrogen up-take is complete, the autoclave is cooled and rendered inert with nitrogen. The catalyst is filtered off and washed with toluene. After working up by distillation, 18.0 g of 3,4-dichloroaniline (yield 96.8% of theory) are obtained.

$^1$H-NMR ($CDCl_3$, 250MHz): 3.72 ppm (s,2H); 6.5 ppm (m,1H); 6.77 ppm (m, 1H); 7.18 ppm (m, 1H).

We claim:

1. Process for the production of an aromatic halogen-amino compound by means of catalytic hydrogenation on a noble metal catalyst of a corresponding aromatic halonitro compound, characterised in that hydrogenation is carried out in the presence of a rhodium, ruthenium, iridium, platinum or palladium catalyst which is modified with an inorganic or organic phosphorus compound with a degree of oxidation of less than 5, and in the presence of a vanadium compound.

2. Process according to claim 1, characterised in that the noble metal catalyst employed is a platinum or indium catalyst.

3. Process according to claim 1, characterised in that the noble metal catalyst is used in a quantity of 0.1 to 10% by weight, based on the aromatic halonitro compound employed.

4. Process according to claim 1, characterised in that the noble metal catalyst in metallised or oxidised form is applied to a carrier.

5. Process according to claim 1, characterised in that the modifying phosphorus compounds are selected from the group phosphines $P(R_a)_{3-n}(H)_n$, phosphinous acids HO—P$(H)_m(R_a)_{2-m}$, phosphine oxides $O=P(R_a)_{3-n}(H)_n$, hypophosphonous acids

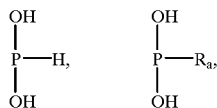

hypophosphorous acids $O=P(OH)(H)_m(R_a)_{2-m}$ and phosphorous acids $O=P(OH)_2H$ or $O=P(OH)_2R_a$, wherein $R_a$ signifies linear or branched $C_1$–$C_{12}$-alkyl or $C_6$–$C_{16}$-aryl, m is 0, 1 or 2, and n is 0, 1, 2 or 3, as well as the salts, esters and amides of the acids.

6. Process according to claim 5, characterised in that the modifying phosphorus compound employed is phosphorous acid and its salts, esters or amides, as well as hypophosphorous acid and its salts, esters or amides.

7. Process according to claim 1, characterised in that modification of the noble metal catalyst with the phosphorus compound takes place in situ prior to hydrogenation.

8. Process according to claim 1, characterised in that the ratio of noble metal in the noble metal catalyst to modifying phosphorus compound is 1:0.1 to 1:1000 molar parts.

9. Process according to claim 1, characterised in that the ratio of noble metal in the noble metal catalyst to modifying phosphorus compound is 1:1 to 1:100 molar parts.

10. Process according to claim 1, characterised in that a vanadium compound is used, which is selected from the group vanadium(III) acetyl acetonate, vanadium(IV) oxyacetyl acetonate, $V_2O_5$, $VOCl_3$, $VCl_6^-$, $[VO(SCN)_4]^{2-}$, $VOSO_4$, $NH_4VO_3$, $LiVO_3$, $NaVO_3$, $KVO_3$, $VCl_3$, $VCl_2$ or the corresponding halides with F or Br.

11. Process according to claim 1, characterised in that ammonium, Li, Na or K vanadate is used, or a hydrate of these vanadates.

12. Process according to claim 1, characterised in that vanadium(III) acetyl acetonate or vanadium(IV)oxyacetyl acetonate is used.

13. Process according to claim 1, characterised in that the molar ratio of noble metal in the noble metal catalyst to vanadium compound is 1:0.1 to 1:1000.

14. Process according to claim 1, characterised in that the process is carried out at a pressure of 1 to 100 bar.

15. Process according to claim 1, characterised in that the process is carried out at a temperature of 0° C. to +160° C.

16. Process according to claim 1, characterised in that the aromatic halonitro compound corresponds to formula I

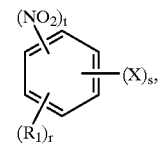

(I)

wherein $R_1$ signifies hydrogen, $C_1$–$C_{12}$-alkyl, $C_1$–$C_{12}$-halogen-alkyl, $C_6$–$C_{16}$-halogen-aryl, $C_3$–$C_{16}$-halogen-heteroaryl, $C_1$–$C_4$-alkylphenyl, $C_1$–$C_4$-alkoxyphenyl, halogen-$C_1$–$C_4$-alkylphenyl, halogen-$C_1$–$C_4$-alkoxyphenyl, $C_1$–$C_{12}$-hydroxyalkyl, $C_3$–$C_8$-cycloalkyl, $C_3$–$C_8$-cycloalkyl substituted by $C_1$–$C_4$-alkyl, $C_6$–$C_{16}$-aryl, $C_7$–$C_{16}$-aralkyl, $C_3$–$C_6$-heterocycloalkyl, $C_3$–$C_{16}$-heteroaryl, $C_4$–$C_{16}$-heteroaralkyl, $SO_3H$, $SO_2R_2$, $SO_2N(R_2)_2$, or a group-$Y_1R_2$;

$Y_1$ signifies $NR_2$, oxygen or sulphur;

$R_2$ signifies hydrogen, $C_1$–$C_{12}$-alkyl, $C_1$–$C_{12}$-halogen-alkyl, $C_6$–$C_1$-halogen-aryl, $C_3$–$C_{16}$-halogen-heteroaryl, $C_1$–$C_4$-alkylphenyl, $C_1$–$C_4$-alkoxyphenyl, halogen-$C_1$–$C_4$-alkylphenyl, halogen-$C_1$–$C_4$-alkylphenyl, halogen-$C_1$–$C_4$-alkoxyphenyl, $C_1$–$C_{12}$-hydroxyalkyl, $C_3$–$C_8$-cycloalkyl, $C_6$–$C_{16}$-aryl, $C_7$–$C_{16}$-aralkyl, $C_3$–$C_6$-heterocycloalkyl, $C_3$–$C_{16}$-heteroaryl, $C_4$–$C_6$-heteroaralkyl;

X signifies fluorine, chlorine, bromine or iodine; and r,s and t, independently of one another, signify a number 1, 2 or 3, whereby r+s+t is less than or equal to six.

* * * * *